United States Patent
Kroon et al.

(10) Patent No.: US 11,319,559 B2
(45) Date of Patent: May 3, 2022

(54) PROCESS FOR ENZYMATIC HYDROLYSIS OF LIGNOCELLULOSIC MATERIAL AND FERMENTATION OF SUGARS

(71) Applicant: DSM IP ASSETS B.V., Heerlen (NL)

(72) Inventors: Johannes Augustinus Kroon, Echt (NL); Pierre Louis Woestenborghs, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 16/754,334

(22) PCT Filed: Oct. 8, 2018

(86) PCT No.: PCT/EP2018/077255
§ 371 (c)(1),
(2) Date: Apr. 7, 2020

(87) PCT Pub. No.: WO2019/072732
PCT Pub. Date: Apr. 18, 2019

(65) Prior Publication Data
US 2020/0332319 A1    Oct. 22, 2020

(30) Foreign Application Priority Data
Oct. 9, 2017 (EP) ..................... 17195379

(51) Int. Cl.
C12P 7/00 (2006.01)
C12P 7/10 (2006.01)
C12P 19/14 (2006.01)

(52) U.S. Cl.
CPC .................. *C12P 7/10* (2013.01); *C12P 19/14* (2013.01); *C12Y 302/01004* (2013.01); *C12Y 302/01021* (2013.01); *C12Y 302/01032* (2013.01); *C12Y 302/01091* (2013.01)

(58) Field of Classification Search
None
See application file for complete search history.

(56) References Cited

U.S. PATENT DOCUMENTS

| 5,364,978 A * | 11/1994 | Kroon | C07C 37/56 568/800 |
| 10,150,843 B2 * | 12/2018 | Carroll | C07C 51/43 |
| 2010/0044210 A1 | 2/2010 | Robinson | |
| 2015/0299089 A1 * | 10/2015 | Parton | C07C 51/00 252/182.12 |

FOREIGN PATENT DOCUMENTS

| WO | 2008/008793 A2 | 1/2008 |
| WO | 2012/130120 A1 | 10/2012 |
| WO | 2016/145350 A1 | 9/2016 |

OTHER PUBLICATIONS

Ahi, Mohsen et al., "Optimization of Sugarcane Bagasse Hydrolysis by Microwave-Assisted Pretreatment for Bioethanol Production", Chemical Engineering and Technology, Oct. 23, 2013, pp. 1997-2005, vol. 36, No. 11.
Tatijarern, Patomwat et al., "Capability of Thai Mission grass (*Pennisetum polystachyon*) as a new weedy lignocellulosic feedstock for production of monomeric sugar", Bioresource Technology, 2013, pp. 423-430, vol. 143.
Kumar, S. et al., "Recent advances in production of bioethanol from lignocellulosic biomass", Chemical Engineering & Technology, Mar. 19, 2009, pp. 517-526, vol. 32, No. 4.
International Search Report of International Patent Application No. PCT/EP2018/077255 dated Feb. 1, 2019.

* cited by examiner

*Primary Examiner* — Hope A Robinson
(74) *Attorney, Agent, or Firm* — McBee Moore & Vanik IP, LLC; Susan McBee; Chester Moore

(57) ABSTRACT

The invention relates to a process for the preparation of a sugar and/or fermentation product from lignocellulosic material.

18 Claims, No Drawings

PROCESS FOR ENZYMATIC HYDROLYSIS OF LIGNOCELLULOSIC MATERIAL AND FERMENTATION OF SUGARS

CROSS-REFERENCE TO RELATED APPLICATIONS

This application is a National Stage entry of International Application No. PCT/EP2018/077255, filed 8 Oct. 2018, which claims priority to European Patent Application No. 17195379.7, filed 9 Oct. 2017.

BACKGROUND

Field

The application relates to a process for preparing a sugar product from lignocellulosic material by enzymatic hydrolysis and a process for preparing a fermentation product by fermentation of sugars.

Description of Related Art

Lignocellulosic material is primarily composed of cellulose, hemicellulose and lignin and provides an attractive platform for generating alternative energy sources to fossil fuels. The material is available in large amounts and can be converted into valuable products e.g. sugars or biofuel, such as bioethanol.

Producing fermentation products from lignocellulosic material is known in the art and generally includes the steps of pretreatment, hydrolysis, fermentation, and optionally recovery of the fermentation products.

During the hydrolysis, which may comprise the steps of liquefaction, presaccharification and/or saccharification, cellulose present in the lignocellulosic material is partly (typically 30 to 95%, dependable on enzyme activity and hydrolysis conditions) converted into sugars by cellulolytic enzymes. The hydrolysis typically takes place during a process lasting 6 to 168 hours (see Kumar, S., Chem. Eng. Technol. 32 (2009), 517-526) under elevated temperatures of 45 to 50° C. and non-sterile conditions.

Commonly, the sugars are then converted into valuable fermentation products such as ethanol by microorganisms like yeast. The fermentation takes place in a separate, preferably anaerobic, process step, either in the same or in a different vessel. The temperature during fermentation is adjusted to 30 to 33° C. to accommodate growth and ethanol production by microorganisms, commonly yeasts. During the fermentation process, the remaining cellulosic material is converted into sugars by the enzymes already present from the hydrolysis step, while microbial biomass and ethanol are produced. The fermentation is finished once the cellulosic material is converted into fermentable sugars and all fermentable sugars are converted into ethanol, carbon dioxide and microbial biomass. This may take up to 6 days. In general, the overall process time of hydrolysis and fermentation may amount up to 13 days.

In general, cost of enzyme production is a major cost factor in the overall production process of fermentation products from lignocellulosic material (see Kumar, S., Chem. Eng. Technol. 32 (2009), 517-526). Thus far, reduction of enzyme production costs is achieved by applying enzyme products from a single or from multiple microbial sources (see WO 2008/008793) with broader and/or higher (specific) hydrolytic activity. This leads to a lower enzyme need, faster conversion rates and/or higher conversion yields and thus to lower overall production costs.

Next to the optimization of enzymes, optimization of process design is a crucial tool to reduce overall costs of the production of sugar products and fermentation products. For example, sugar loss by means of sugar degradation products increases with decreasing yield. Since sugar degradation products can inhibit fermentation, process design should be optimized to decrease the amount of these sugar degradation products.

For economic reasons, it is therefore desirable to include new and innovative process configurations aimed at reducing overall production costs in the process involving pretreatment, hydrolysis and fermentation of lignocellulosic material.

SUMMARY

An object of the application is to provide an improved process for the preparation of a sugar product and/or a fermentation product from lignocellulosic material. The process is improved by using specific pretreatment, hydrolysis and fermentation conditions.

DETAILED DESCRIPTION

Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows. The articles "a" and "an" are used herein to refer to one or to more than one (i.e. to one or at least one) of the grammatical object of the article. By way of example, "an element" may mean one element or more than one element.

The present application relates to process for the preparation of a sugar product from lignocellulosic material, comprising the following steps: (a) pretreating the lignocellulosic material at a temperature of 160° C. to 200° C. at a pH of 1.0 to 2.5 for 1 to 15 minutes; (b) enzymatically hydrolysing the pretreated lignocellulosic material having a dry matter weight of 15 to 25% (w/w) at a temperature of 50° C. to 65° C. and a pH of 4 to 6 for 40 hours to 150 hours using a whole fermentation broth of a filamentous fungus, said broth comprising at least a cellobiohydrolase, an endoglucanase, a beta-glucosidase, a xylanase, a beta-xylosidase, and a lytic monosaccharide oxygenase; and (c) optionally, recovering the sugar product. The term "sugar product", "one or more sugars" or "sugar" are used interchangeably herein. Alternatively, the term "hydrolysed lignocellulosic material" can be used instead of these terms.

The present application also relates to a process for the preparation of a fermentation product from lignocellulosic material, comprising the steps of (a) performing a process for the preparation of a sugar product from lignocellulosic material as described herein, (b) fermenting the sugar product to obtain the fermentation product, and (c) optionally, recovering the fermentation product. In an embodiment the present application relates to a process for the preparation of a fermentation product from lignocellulosic material, comprising the following steps: (a) pretreating the lignocellulosic material at a temperature of 160° C. to 200° C. at a pH of 1.0 to 2.5 for 1 to 15 minutes; (b) enzymatically hydrolysing the pretreated lignocellulosic material having a dry matter weight of 15 to 25% (w/w) at a temperature of 50° C.

to 65° C. and a pH of 4 to 6 for 40 hours to 150 hours using a whole fermentation broth of a filamentous fungus, said broth comprising at least a cellobiohydrolase, an endoglucanase, a beta-glucosidase, a xylanase, a beta-xylosidase and a lytic monosaccharide oxygenase, to obtain a hydrolysed lignocellulosic material; (c) fermenting the hydrolysed lignocellulosic material to produce a fermentation product; and (d) optionally, recovering the fermentation product.

In an embodiment the enzymatic hydrolysis is done in a reactor. In an embodiment the enzymatic hydrolysis may also be done in two, three, four, five, six, seven, eight, nine, ten or even more reactors. So, the term "reactor" is not limited to a single reactor, but may mean multiple reactors.

In the processes as described herein, pretreated lignocellulosic material is added to the reactor in which the enzymatic hydrolysis takes place. This can be done batch-wise, fed-batch wise or continuously. In an embodiment an enzyme composition is added to the reactor in which the enzymatic hydrolysis takes place. This can be done batch-wise, fed-batch wise or continuously. The enzyme composition may be an aqueous composition. In an embodiment hydrolysed lignocellulosic material and/or partly hydrolysed lignocellulosic material is recycled back to the reactor in which the enzymatic hydrolysis takes place. In an embodiment the hydrolysed lignocellulosic material and/or partly hydrolysed lignocellulosic material is cooled before addition to the reactor in which the enzymatic hydrolysis takes place. In an embodiment the hydrolysed lignocellulosic material and/or partly hydrolysed lignocellulosic material is subjected to a solid/liquid separation before addition to the reactor in which the enzymatic hydrolysis takes place. In an embodiment the solid/liquid separation is done before the cooling step. In an embodiment only the liquid fraction obtained after the solid/liquid separation is cooled. In an embodiment both the liquid fraction and the solid fraction are added to the reactor in which the enzymatic hydrolysis takes place.

In an embodiment the total enzymatic hydrolysis time is 10 hours or more, 12 hours or more, 14 hours or more, 16 hours or more, 18 hours or more, 20 hours or more, 30 hours or more, 40 hours or more, 50 hours or more, 60 hours or more, 70 hours or more, 80 hours or more, 90 hours or more, 100 hours or more, 110 hours or more, 120 hours or more, 130 hours or more, 140 hours or more, 150 hours or more, 160 hours or more, 170 hours or more, 180 hours or more, 190 hours or more, 200 hours or more. In an embodiment the enzymatic hydrolysis time is 40 to 150 hours.

In an embodiment oxygen is added to the pretreated lignocellulosic material during enzymatic hydrolysis. In an embodiment oxygen is added during at least a part of the enzymatic hydrolysis. Oxygen can be added continuously or discontinuously during enzymatic hydrolysis. In an embodiment oxygen is added one or more times during the process for the preparation of a sugar product from lignocellulosic material as described herein. In an embodiment oxygen may be added during pretreatment, during addition of (pretreated) lignocellulosic material to a reactor, during addition of enzyme to a reactor, during addition of hydrolysed lignocellulosic material and/or partly hydrolysed lignocellulosic material to a reactor, during cooling of hydrolysed lignocellulosic material and/or partly hydrolysed lignocellulosic material, during solid/liquid separation of hydrolysed lignocellulosic material and/or partly hydrolysed lignocellulosic material or any combination thereof. Oxygen is added to the reactors used in the enzymatic hydrolysis.

Oxygen can be added in several forms. For example, oxygen can be added as oxygen gas, oxygen-enriched gas, such as oxygen-enriched air, or air. Oxygen may also be added by means of in situ oxygen generation.

Examples how to add oxygen include, but are not limited to, addition of oxygen by means of sparging, blowing, electrolysis, chemical addition of oxygen, filling a reactor used in the enzymatic hydrolysis from the top (plunging the hydrolysate into the reactor and consequently introducing oxygen into the hydrolysate) and addition of oxygen to the headspace of a reactor. When oxygen is added to the headspace of the reactor, sufficient oxygen necessary for the hydrolysis reaction may be supplied. In general, the amount of oxygen added to the reactor can be controlled and/or varied. Restriction of the oxygen supplied is possible by adding only oxygen during part of the hydrolysis time in the reactor. Another option is adding oxygen at a low concentration, for example by using a mixture of air and recycled air (air leaving the reactor) or by "diluting" air with an inert gas. Increasing the amount of oxygen added can be achieved by addition of oxygen during longer periods of the hydrolysis time, by adding the oxygen at a higher concentration or by adding more air. Another way to control the oxygen concentration is to add an oxygen consumer and/or an oxygen generator. Oxygen can be introduced into the (pretreated) lignocellulosic material present in the reactor. It can also be introduced into the headspace of the reactor. Oxygen can be blown into the (pretreated) lignocellulosic material present in the reactor. It can also be blown into the headspace of the reactor.

In an embodiment oxygen is added to the reactor used in the enzymatic hydrolysis before and/or during and/or after the addition of the pretreated lignocellulosic material to the reactor. The oxygen may be introduced together with the pretreated lignocellulosic material that enters the reactor. The oxygen may be introduced into the material stream that will enter the reactor or with part of the reactor contents that passes an external loop of the reactor. Preferably, oxygen is added when the (pretreated) lignocellulosic material is present in the reactor.

In an embodiment the enzymatic hydrolysis is done in a reactor having a volume of 10-5000 m$^3$, preferably of 50-5000 m$^3$. In case multiple reactors are used in the enzymatic hydrolysis of the processes as described herein, they may have the same volume, but also may have a different volume.

In an embodiment the reactor in which the enzymatic hydrolysis is done has a ratio height to diameter of 2:1 to 8:1.

In an embodiment the pretreatment is done in a reactor having a volume of 30-200 m$^3$, preferably of 100-150 m$^3$. In case multiple reactors are used in the pretreatment of the processes as described herein, they may have the same volume, but also may have a different volume.

In an embodiment the pretreatment reactor used in the processes as described herein has a ratio height to diameter of 3:1 to 12:1.

In an embodiment the enzyme composition used in the liquefaction step and/or the saccharification step of the processes as described herein is from a fungus, preferably a filamentous fungus. In an embodiment the enzymes in the enzyme composition are derived from a fungus, preferably a filamentous fungus or the enzymes comprise a fungal enzyme, preferably a filamentous fungal enzyme. The enzymes used in the enzymatic hydrolysis of the processes as described herein are derived from a fungus or the enzymes used in the enzymatic hydrolysis of the processes as described herein comprise a fungal enzyme. "Filamentous fungi" include all filamentous forms of the subdivision *Eumycota* and *Oomycota* (as defined by Hawksworth et al., In, Ainsworth and Bisby's Dictionary of The Fungi, 8th edition, 1995, CAB International, University Press, Cambridge, UK). Filamentous fungi include, but are not limited to *Acremonium, Agaricus, Aspergillus, Aureobasidium, Beauvaria, Cephalosporium, Ceriporiopsis, Chaetomium paecilomyces, Chrysosporium, Claviceps, Cochiobolus, Coprinus, Cryptococcus, Cyathus, Emericella, Endothia, Endothia mucor, Filibasidium, Fusarium, Geosmithia, Gilocladium, Humicola, Magnaporthe, Mucor, Myceliophthora, Myrothecium, Neocaffimastix, Neurospora, Paecilomyces, Penicillium, Piromyces, Panerochaete, Pleurotus, Podospora, Pyricularia, Rasamsonia, Rhizomucor, Rhizopus, Scylatidium, Schizophyllum, Stagonospora, Talaromyces, Thermoascus, Thermomyces, Thielavia, Tolypocladium, Trametes pleurotus, Trichoderma* and *Trichophyton*. In a preferred embodiment the fungus is *Rasamsonia*, with *Rasamsonia emersonii* being most preferred. Ergo, the processes as described herein are advantageously applied in combination with enzymes derived from a microorganism of the genus *Rasamsonia* or the enzymes used in the processes as described herein comprise a *Rasamsonia* enzyme.

Several strains of filamentous fungi are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Preferably, the processes as described herein are done with thermostable enzymes. "Thermostable" enzyme as used herein means that the enzyme has a temperature optimum of 50° C. or higher, 60° C. or higher, 70° C. or higher, 75° C. or higher, 80° C. or higher, or even 85° C. or higher. They may for example be isolated from thermophilic microorganisms or may be designed by the skilled person and artificially synthesized. In one embodiment the polynucleotides encoding the thermostable enzymes may be isolated or obtained from thermophilic or thermotolerant filamentous fungi or isolated from non-thermophilic or non-thermotolerant fungi, but are found to be thermostable. By "thermophilic fungus" is meant a fungus that grows at a temperature of 50° C. or higher. By "themotolerant" fungus is meant a fungus that grows at a temperature of 45° C. or higher, having a maximum near 50° C.

Suitable thermophilic or thermotolerant fungal cells may be *Humicola, Rhizomucor, Myceliophthora, Rasamsonia, Talaromyces, Thermomyces, Thermoascus* or *Thielavia* cells, preferably *Rasamsonia* cells. Preferred thermophilic or thermotolerant fungi are *Humicola grisea var. thermoidea, Humicola lanuginosa, Myceliophthora thermophila, Papulaspora thermophilia, Rasamsonia byssochlamydoides, Rasamsonia emersonii, Rasamsonia argillacea, Rasamsonia eburnean, Rasamsonia brevistipitata, Rasamsonia cylindrospora, Rhizomucor pusillus, Rhizomucor miehei, Talaromyces bacillisporus, Talaromyces leycettanus, Talaromyces thermophilus, Thermomyces lenuginosus, Thermoascus crustaceus, Thermoascus thermophilus Thermoascus aurantiacus* and *Thielavia terrestris*.

*Rasamsonia* is a new genus comprising thermotolerant and thermophilic *Talaromyces* and *Geosmithia* species. Based on phenotypic, physiological and molecular data, the species *Talaromyces emersonii, Talaromyces byssochlamydoides, Talaromyces eburneus, Geosmithia argillacea* and *Geosmithia cylindrospora* were transferred to *Rasamsonia* gen. nov. *Talaromyces emersonii, Penicillium geosmithia emersonii* and *Rasamsonia emersonii* are used interchangeably herein.

In the processes as described herein enzyme compositions are used. In an embodiment the compositions are stable. "Stable enzyme compositions" as used herein means that the enzyme compositions retain activity after 30 hours of hydrolysis reaction time, preferably at least 10%, 20%, 30%, 40%, 50%, 60%, 65%, 70%, 75%, 80% 85%, 90%, 95%, 96%, 97%, 98%, 99% or 100% of its initial activity after 30 hours of hydrolysis reaction time. In an embodiment the enzyme composition retains activity after 40, 50, 60, 70, 80, 90 100, 150, 200, 250, 300, 350, 400, 450, 500 hours of hydrolysis reaction time.

The enzymes may be prepared by fermentation of a suitable substrate with a suitable microorganism, e.g. *Rasamsonia emersonii* or *Aspergillus niger*, wherein the enzymes are produced by the microorganism. The microorganism may be altered to improve or to make the enzymes. For example, the microorganism may be mutated by classical strain improvement procedures or by recombinant DNA techniques. Therefore, the microorganisms mentioned herein can be used as such to produce the enzymes or may be altered to increase the production or to produce altered enzymes which might include heterologous enzymes, e.g. cellulases, thus enzymes that are not originally produced by that microorganism. Preferably, a fungus, more preferably a filamentous fungus is used to produce the enzymes. Advantageously, a thermophilic or thermotolerant microorganism is used. Optionally, a substrate is used that induces the expression of the enzymes by the enzyme producing microorganism.

The enzymes are used to liquefy the lignocellulosic material and/or release sugars from lignocellulosic material that comprises polysaccharides. The major polysaccharides are celluloses (glucans) and hemicelluloses (xylans, heteroxylans and xyloglucans). In addition, some hemicellulose may be present as glucomannans, for example in wood-derived lignocellulosic material. The enzymatic hydrolysis of these polysaccharides to soluble sugars, including both monomers and multimers, for example glucose, cellobiose, xylose, arabinose, galactose, fructose, mannose, rhamnose, ribose, galacturonic acid, glucuronic acid and other hexoses and pentoses occurs under the action of different enzymes acting in concert. A sugar product comprises soluble sugars, including both monomers and multimers. In an embodiment the sugar product and/or hydrolysed lignocellulosic material comprises glucose, galactose and arabinose. Examples of other sugars are cellobiose, xylose, arabinose, galactose, fructose, mannose, rhamnose, ribose, galacturonic acid, glucoronic acid and other hexoses and pentoses. The sugar product may be used as such or may be further processed for example recovered and/or purified.

In addition, pectins and other pectic substances such as arabinans may make up considerably proportion of the dry mass of typically cell walls from non-woody plant tissues (about a quarter to half of dry mass may be pectins). Furthermore, the lignocellulosic material may comprise lignin.

Enzymes that may be used in the processes as described herein are described in more detail below.

Lytic polysaccharide monooxygenases, endoglucanases (EG) and exo-cellobiohydrolases (CBH) catalyze the hydrolysis of insoluble cellulose to products such as cellooligosaccharides (cellobiose as a main product), while β-glucosidases (BG) convert the oligosaccharides, mainly cellobiose and cellotriose, to glucose.

Xylanases together with other accessory enzymes, for example α-L-arabinofuranosidases, feruloyl and acetylxylan esterases, glucuronidases, and β-xylosidases catalyze the hydrolysis of hemicellulose.

An enzyme composition for use in the processes as described herein may comprise at least two activities, although typically a composition will comprise more than two activities, for example, three, four, five, six, seven, eight, nine or even more activities. Typically, an enzyme composition for use in the processes as described herein comprises at least two cellulases. The at least two cellulases may contain the same or different activities. The enzyme composition for use in the processes as described herein may also comprises at least one enzyme other than a cellulase. Preferably, the at least one other enzyme has an auxiliary enzyme activity, i.e. an additional activity which, either directly or indirectly leads to lignocellulose degradation. Examples of such auxiliary activities are mentioned herein and include, but are not limited to hemicellulases.

An enzyme composition for use in the processes as described herein at least comprises a lytic polysaccharide monooxygenase (LPMO), an endoglucanase (EG), a cellobiohydrolase (CBH), a xylanase, a beta-xylosidase (BX) and a beta-glucosidase (BG). An enzyme composition may comprise more than one enzyme activity per activity class. For example, a composition may comprise two endoglucanases, for example an endoglucanase having endo-1,3(1,4)-β glucanase activity and an endoglucanase having endo-β-1,4-glucanase activity.

A composition for use in the processes as described herein may be derived from a fungus, such as a filamentous fungus, such as *Rasamsonia*, such as *Rasamsonia emersonii*. In an embodiment at least one of enzymes may be derived from *Rasamsonia emersonii*. In an embodiment the lytic polysaccharide monooxygenase and/or the beta-xylosidase are derived from *Rasamsonia emersonii*. If needed, the enzyme can be supplemented with additional enzymes from other sources. Such additional enzymes may be derived from classical sources and/or produced by genetically modified organisms.

In addition, enzymes in the enzyme compositions for use in the processes as described herein may be able to work at low pH. For the purposes of this invention, low pH indicates a pH of 5.5 or lower, 5 or lower, 4.9 or lower, 4.8 or lower, 4.7 or lower, 4.6 or lower, 4.5 or lower, 4.4 or lower, 4.3 or lower, 4.2 or lower, 4.1 or lower, 4.0 or lower 3.9 or lower, 3.8 or lower, 3.7 or lower, 3.6 or lower, 3.5 or lower.

The enzyme composition for use in the processes as described herein may comprise a cellulase and/or a hemicellulase and/or a pectinase from *Rasamsonia*. They may also comprise a cellulase and/or a hemicellulase and/or a pectinase from a source other than *Rasamsonia*. They may be used together with one or more *Rasamsonia* enzymes or they may be used without additional *Rasamsonia* enzymes being present.

An enzyme composition for use in the processes as described herein comprises a lytic polysaccharide monooxygenase, an endoglucanase, a cellobiohydrolase I (CBHI), a cellobiohydrolase II (CBHII), a beta-glucosidase, an endoxylanase (EX) and a beta-xylosidase.

An enzyme composition for use in the processes as described herein may comprise one type of cellulase activity and/or hemicellulase activity and/or pectinase activity provided by a composition as described herein and a second type of cellulase activity and/or hemicellulase activity and/ or pectinase activity provided by an additional cellulase/ hemicellulase/pectinase.

As used herein, a cellulase is any polypeptide which is capable of degrading or modifying cellulose. A polypeptide which is capable of degrading cellulose is one which is capable of catalyzing the process of breaking down cellulose into smaller units, either partially, for example into cellodextrins, or completely into glucose monomers. A cellulase as described herein may give rise to a mixed population of cellodextrins and glucose monomers. Such degradation will typically take place by way of a hydrolysis reaction.

As used herein, a hemicellulase is any polypeptide which is capable of degrading or modifying hemicellulose. That is to say, a hemicellulase may be capable of degrading or modifying one or more of xylan, glucuronoxylan, arabinoxylan, glucomannan and xyloglucan. A polypeptide which is capable of degrading a hemicellulose is one which is capable of catalyzing the process of breaking down the hemicellulose into smaller polysaccharides, either partially, for example into oligosaccharides, or completely into sugar monomers, for example hexose or pentose sugar monomers. A hemicellulase as described herein may give rise to a mixed population of oligosaccharides and sugar monomers. Such degradation will typically take place by way of a hydrolysis reaction.

As used herein, a pectinase is any polypeptide which is capable of degrading or modifying pectin. A polypeptide which is capable of degrading pectin is one which is capable of catalyzing the process of breaking down pectin into smaller units, either partially, for example into oligosaccharides, or completely into sugar monomers. A pectinase as described herein may give rise to a mixed population of oligosacchardies and sugar monomers. Such degradation will typically take place by way of a hydrolysis reaction.

Accordingly, an enzyme composition for use in the processes as described herein may comprise one or more of the following enzymes, a lytic polysaccharide monooxygenase (e.g. GH61), a cellobiohydrolase, an endo-β-1,4-glucanase, a beta-glucosidase, and a β-(1,3)(1,4)-glucanase. A composition for use in the processes as described herein may also comprise one or more hemicellulases, for example, an endoxylanase, a β-xylosidase, a α-L-arabinofuranosidase, an α-D-glucuronidase, an acetyl xylan esterase, a feruloyl esterase, a coumaroyl esterase, an α-galactosidase, a β-galactosidase, a β-mannanase and/or a β-mannosidase. A composition for use in the processes as described herein may also comprise one or more pectinases, for example, an endo-polygalacturonase, a pectin-methyl esterase, an endo-galactanase, a beta-galactosidase, a pectin-acetyl esterase, an endo-pectin lyase, pectate lyase, alpha-rhamnosidase, an exo-galacturonase, an expolygalacturonate lyase, a rhamnogalacturonan hydrolase, a rhamnogalacturonan lyase, a rhamnogalacturonan acetyl esterase, a rhamnogalacturonan galacturonohydrolase, and/or a xylogalacturonase. In addition, one or more of the following enzymes, an amylase, a protease, a lipase, a ligninase, a hexosyltransferase, a glucuronidase, an expansin, a cellulose induced protein or a cellulose integrating protein or like protein may be present in a composition for use in the processes as described herein (these are referred to as auxiliary activities above).

As used herein, lytic polysaccharide monooxygenases are enzymes that have recently been classified by CAZy in family AA9 (Auxiliary Activity Family 9) or family AA10 (Auxiliary Activity Family 10). Ergo, there exist AA9 lytic polysaccharide monooxygenases and AA10 lytic polysaccharide monooxygenases. Lytic polysaccharide monooxygenases are able to open a crystalline glucan structure and enhance the action of cellulases on lignocellulose substrates. They are enzymes having cellulolytic enhancing activity.

Lytic polysaccharide monooxygenases may also affect cello-oligosaccharides. According to the latest literature, (see Isaksen et al., Journal of Biological Chemistry, vol. 289, no. 5, p. 2632-2642), proteins named GH61 (glycoside hydrolase family 61 or sometimes referred to EGIV) are lytic polysaccharide monooxygenases. GH61 was originally classified as endoglucanase based on measurement of very weak endo-1,4-I3-d-glucanase activity in one family member, but have recently been reclassified by CAZy in family AA9. CBM33 (family 33 carbohydrate-binding module) is also a lytic polysaccharide monooxygenase (see Isaksen et al, Journal of Biological Chemistry, vol. 289, no. 5, pp. 2632-2642). CAZy has recently reclassified CBM33 in the AA10 family.

In an embodiment the lytic polysaccharide monooxygenase comprises an AA9 lytic polysaccharide monooxygenase. This means that at least one of the lytic polysaccharide monooxygenases in the enzyme composition is an AA9 lytic polysaccharide monooxygenase. In an embodiment all lytic polysaccharide monooxygenases in the enzyme composition are AA9 lytic polysaccharide monooxygenase.

In an embodiment the enzyme composition comprises a lytic polysaccharide monooxygenase from *Thermoascus*, such as *Thermoascus aurantiacus*, such as the one described in WO 2005/074656 as SEQ ID NO:2 and SEQ ID NO:1 in WO2014/130812 and in WO 2010/065830; or from *Thielavia*, such as *Thielavia terrestris*, such as the one described in WO 2005/074647 as SEQ ID NO: 8 or SEQ ID NO:4 in WO2014/130812 and in WO 2008/148131, and WO 2011/035027; or from *Aspergillus*, such as *Aspergillus fumigatus*, such as the one described in WO 2010/138754 as SEQ ID NO:2 or SEQ ID NO: 3 in WO2014/130812; or from *Penicillium*, such as *Penicillium emersonii*, such as the one disclosed as SEQ ID NO:2 in WO 2011/041397 or SEQ ID NO:2 in WO2014/130812. Other suitable lytic polysaccharide monooxygenases include, but are not limited to, *Trichoderma reesei* (see WO 2007/089290), *Myceliophthora thermophila* (see WO 2009/085935, WO 2009/085859, WO 2009/085864, WO 2009/085868), *Penicillium pinophilum* (see WO 2011/005867), *Thermoascus* sp. (see WO 2011/039319), and *Thermoascus crustaceous* (see WO 2011/041504). Other cellulolytic enzymes that may be comprised in the enzyme composition are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. No. 5,457,046, U.S. Pat. No. 5,648,263, and U.S. Pat. No. 5,686,593, to name just a few. In a preferred embodiment, the lytic polysaccharide monooxygenase is from *Rasamsonia*, e.g. *Rasamsonia emersonii* (see WO 2012/000892).

As used herein, endoglucanases are enzymes which are capable of catalyzing the endohydrolysis of 1,4-β-D-glucosidic linkages in cellulose, lichenin or cereal β-D-glucans. They belong to EC 3.2.1.4 and may also be capable of hydrolyzing 1,4-linkages in β-D-glucans also containing 1,3-linkages. Endoglucanases may also be referred to as cellulases, avicelases, endoglucan hydrolases, β-1,4-glucanases, carboxymethyl cellulases, celludextrinases, endo-1, 4-β-D-glucanases, endo-1,4-β-D-glucanohydrolases or endo-1,4-β-glucanases.

In an embodiment the endoglucanase comprises a GH5 endoglucanase and/or a GH7 endoglucanase. This means that at least one of the endoglucanases in the enzyme composition is a GH5 endoglucanase or a GH7 endoglucanase. In case there are more endoglucanases in the enzyme composition, these endoglucanases can be GH5 endoglucanases, GH7 endoglucanases or a combination of GH5 endoglucanases and GH7 endoglucanases. In a preferred embodiment the endoglucanase comprises a GH5 endoglucanase.

In an embodiment the enzyme composition comprises an endoglucanase from *Trichoderma*, such as *Trichoderma reesei*; from *Humicola*, such as a strain of *Humicola insolens*; from *Aspergillus*, such as *Aspergillus aculeatus* or *Aspergillus kawachii*; from *Erwinia*, such as *Erwinia carotovara*; from *Fusarium*, such as *Fusarium oxysporum*; from *Thielavia*, such as *Thielavia terrestris*; from *Humicola*, such as *Humicola grisea var.* thermoidea or *Humicola insolens*; from *Melanocarpus*, such as *Melanocarpus albomyces*; from *Neurospora*, such as *Neurospora crassa*; from *Myceliophthora*, such as *Myceliophthora thermophila*; from *Cladorrhinum*, such as *Cladorrhinum foecundissimum*; and/or from *Chrysosporium*, such as a strain of *Chrysosporium lucknowense*. In a preferred embodiment the endoglucanase is from *Rasamsonia*, such as a strain of *Rasamsonia emersonii* (see WO 01/70998). In an embodiment even a bacterial endoglucanase can be used including, but are not limited to, *Acidothermus cellulolyticus* endoglucanase (see WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (see WO 05/093050); and *Thermobifida fusca* endoglucanase V (see WO 05/093050).

As used herein, beta-xylosidases (EC 3.2.1.37) are polypeptides which are capable of catalysing the hydrolysis of 1,4-β-D-xylans, to remove successive D-xylose residues from the non-reducing termini. Beta-xylosidases may also hydrolyze xylobiose. Beta-xylosidase may also be referred to as xylan 1,4-β-xylosidase, 1,4-β-D-xylan xylohydrolase, exo-1,4-β-xylosidase or xylobiase.

In an embodiment the beta-xylosidase comprises a GH3 beta-xylosidase. This means that at least one of the beta-xylosidases in the enzyme composition is a GH3 beta-xylosidase. In an embodiment all beta-xylosidases in the enzyme composition are GH3 beta-xylosidases.

In an embodiment the enzyme composition comprises a beta-xylosidase from *Neurospora crassa, Aspergillus fumigatus* or *Trichoderma reesei*. In a preferred embodiment the enzyme composition comprises a beta-xylosidase from *Rasamsonia*, such as *Rasamsonia emersonii* (see WO 2014/118360).

As used herein, an endoxylanase (EC 3.2.1.8) is any polypeptide which is capable of catalysing the endohydrolysis of 1,4-β-D-xylosidic linkages in xylans. This enzyme may also be referred to as endo-1,4-β-xylanase or 1,4-β-D-xylan xylanohydrolase. An alternative is EC 3.2.1.136, a glucuronoarabinoxylan endoxylanase, an enzyme that is able to hydrolyze 1,4 xylosidic linkages in glucuronoarabinoxylans.

In an embodiment the endoxylanase comprises a GH10 xylanase. This means that at least one of the endoxylanases in the enzyme composition is a GH10 xylanase. In an embodiment all endoxylanases in the enzyme composition are GH10 xylanases.

In an embodiment the enzyme composition comprises an endoxylanase from *Aspergillus aculeatus* (see WO 94/21785), *Aspergillus fumigatus* (see WO 2006/078256), *Penicillium pinophilum* (see WO 2011/041405), *Penicillium* sp. (see WO 2010/126772), *Thielavia terrestris* NRRL 8126 (see WO 2009/079210), *Talaromyces leycettanus, Thermobifida fusca*, or *Trichophaea saccata* GH10 (see WO 2011/057083). In a preferred embodiment the enzyme composition comprises an endoxylanase from *Rasamsonia*, such as *Rasamsonia emersonii* (see WO 02/24926).

As used herein, a beta-glucosidase (EC 3.2.1.21) is any polypeptide which is capable of catalysing the hydrolysis of terminal, non-reducing β-D-glucose residues with release of β-D-glucose. Such a polypeptide may have a wide specificity forβ-D-glucosides and may also hydrolyze one or more of the following: a β-D-galactoside, an α-L-arabinoside, a β-D-xyloside or a β-D-fucoside. This enzyme may also be referred to as amygdalase, β-D-glucoside glucohydrolase, cellobiase or gentobiase.

In an embodiment the enzyme composition comprises a beta-glucosidase from *Aspergillus*, such as *Aspergillus oryzae*, such as the one disclosed in WO 02/095014 or the fusion protein having beta-glucosidase activity disclosed in WO 2008/057637, or *Aspergillus fumigatus*, such as the one disclosed as SEQ ID NO:2 in WO 2005/047499 or SEQ ID NO:5 in WO 2014/130812 or an *Aspergillus fumigatus* beta-glucosidase variant, such as one disclosed in WO 2012/044915, such as one with the following substitutions: F100D, S283G, N456E, F512Y (using SEQ ID NO: 5 in WO 2014/130812 for numbering), or *Aspergillus aculeatus, Aspergillus niger* or *Aspergillus kawachi*. In another embodiment the beta-glucosidase is derived from *Penicillium*, such as *Penicillium brasilianum* disclosed as SEQ ID NO:2 in WO 2007/019442, or from *Trichoderma*, such as *Trichoderma reesei*, such as ones described in U.S. Pat. Nos. 6,022,725, 6,982,159, 7,045,332, 7,005,289, US 2006/0258554 US 2004/0102619. In an embodiment even a bacterial beta-glucosidase can be used. In another embodiment the beta-glucosidase is derived from *Thielavia terrestris* (WO 2011/035029) or Trichophaea saccata (WO 2007/019442). In a preferred embodiment the enzyme composition comprises a beta-glucosidase from *Rasamsonia*, such as *Rasamsonia emersonii* (see WO 2012/000886).

As used herein, a cellobiohydrolase (EC 3.2.1.91) is any polypeptide which is capable of catalyzing the hydrolysis of 1,4-β-D-glucosidic linkages in cellulose or cellotetraose, releasing cellobiose from the ends of the chains. This enzyme may also be referred to as cellulase 1,4-β-cellobiosidase, 1,4-β-cellobiohydrolase, 1,4-β-D-glucan cellobiohydrolase, avicelase, exo-1,4-β-D-glucanase, exocellobiohydrolase or exoglucanase.

In an embodiment the enzyme composition comprises a cellobiohydrolase I from *Aspergillus*, such as *Aspergillus fumigatus*, such as the Cel7A CBH I disclosed in SEQ ID NO:6 in WO 2011/057140 or SEQ ID NO:6 in WO 2014/130812; from *Trichoderma*, such as *Trichoderma reesei*; from *Chaetomium*, such as *Chaetomium thermophilum*; from *Talaromyces*, such as *Talaromyces leycettanus* or from *Penicillium*, such as *Penicillium emersonii*. In a preferred embodiment the enzyme composition comprises a cellobiohydrolase I from *Rasamsonia*, such as *Rasamsonia emersonii* (see WO 2010/122141).

In an embodiment the enzyme composition comprises a cellobiohydrolase II from *Aspergillus*, such as *Aspergillus fumigatus*, such as the one in SEQ ID NO:7 in WO 201 4/1 3081 2 or from *Trichoderma*, such as *Trichoderma reesei*, or from *Talaromyces*, such as *Talaromyces leycettanus*, or from *Thielavia*, such as *Thielavia terrestris*, such as cellobiohydrolase II CEL6A from *Thielavia terrestris*. In a preferred embodiment the enzyme composition comprises a cellobiohydrolase II from *Rasamsonia*, such as *Rasamsonia emersonii* (see WO 2011/098580).

In an embodiment the enzyme composition also comprises one or more of the below mentioned enzymes.

As used herein, aβ-(1,3)(1,4)-glucanase (EC 3.2.1.73) is any polypeptide which is capable of catalysing the hydrolysis of 1,4-β-D-glucosidic linkages in β-D-glucans containing 1,3- and 1,4-bonds. Such a polypeptide may act on lichenin and cereal β-D-glucans, but not on β-D-glucans containing only 1,3- or 1,4-bonds. This enzyme may also be referred to as licheninase, 1,3-1,4-β-D-glucan 4-glucanohydrolase, β-glucanase, endo-13-1,3-1,4 glucanase, lichenase or mixed linkage β-glucanase. An alternative for this type of enzyme is EC 3.2.1.6, which is described as endo-1,3(4)-beta-glucanase. This type of enzyme hydrolyses 1,3- or 1,4-linkages in beta-D-glucanse when the glucose residue whose reducing group is involved in the linkage to be hydrolysed is itself substituted at C-3. Alternative names include endo-1,3-beta-glucanase, laminarinase, 1,3-(1,3;1,4)-beta-D-glucan 3 (4) glucanohydrolase. Substrates include laminarin, lichenin and cereal beta-D-glucans.

As used herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase. Examples of arabinofuranosidases that may be comprised in the enzyme composition include, but are not limited to, arabinofuranosidases from *Aspergillus niger, Humicola insolens* DSM 1800 (see WO 2006/114094 and WO 2009/073383) and *M. giganteus* (see WO 2006/114094).

As used herein, an α-D-glucuronidase (EC 3.2.1.139) is any polypeptide which is capable of catalysing a reaction of the following form: alpha-D-glucuronoside+H(2)O=an alcohol+D-glucuronate. This enzyme may also be referred to as alpha-glucuronidase or alpha-glucosiduronase. These enzymes may also hydrolyse 4-O-methylated glucoronic acid, which can also be present as a substituent in xylans. An alternative is EC 3.2.1.131: xylan alpha-1,2-glucuronosidase, which catalyses the hydrolysis of alpha-1,2-(4-O-methyl)glucuronosyl links. Examples of alpha-glucuronidases that may be comprised in the enzyme composition include, but are not limited to, alpha-glucuronidases from *Aspergillus clavatus, Aspergillus fumigatus, Aspergillus niger, Aspergillus terreus, Humicola insolens* (see WO 2010/014706), *Penicillium aurantiogriseum* (see WO 2009/068565) and *Trichoderma reesei*.

As used herein, an acetyl xylan esterase (EC 3.1.1.72) is any polypeptide which is capable of catalysing the deacetylation of xylans and xylo-oligosaccharides. Such a polypeptide may catalyze the hydrolysis of acetyl groups from polymeric xylan, acetylated xylose, acetylated glucose, alpha-napthyl acetate or p-nitrophenyl acetate but, typically, not from triacetylglycerol. Such a polypeptide typically does not act on acetylated mannan or pectin. Examples of acetylxylan esterases that may be comprised in the enzyme composition include, but are not limited to, acetylxylan esterases from *Aspergillus aculeatus* (see WO 2010/108918), *Chaetomium globosum, Chaetomium gracile, Humicola insolens* DSM 1800 (see WO 2009/073709), *Hypocrea jecorina* (see WO 2005/001036), *Myceliophtera thermophila* (see WO 2010/014880), *Neurospora crassa, Phaeosphaeria nodorum* and *Thielavia terrestris* NRRL 8126 (see WO 2009/042846). In a preferred embodiment the enzyme composition comprises an acetyl xylan esterase from *Rasamsonia*, such as *Rasamsonia emersonii* (see WO 2010/000888)

As used herein, a feruloyl esterase (EC 3.1.1.73) is any polypeptide which is capable of catalysing a reaction of the form: feruloyl-saccharide+$H_2O$=ferulate+saccharide. The saccharide may be, for example, an oligosaccharide or a polysaccharide. It may typically catalyse the hydrolysis of the 4-hydroxy-3-methoxycinnamoyl (feruloyl) group from an esterified sugar, which is usually arabinose in 'natural' substrates. p-nitrophenol acetate and methyl ferulate are typically poorer substrates. This enzyme may also be referred to as cinnamoyl ester hydrolase, ferulic acid esterase or hydroxycinnamoyl esterase. It may also be referred to as a hemicellulase accessory enzyme, since it may help xylanases and pectinases to break down plant cell wall hemicellulose and pectin. Examples of feruloyl esterases (ferulic acid esterases) that may be comprised in the enzyme composition include, but are not limited to, feruloyl esterases form *Humicola insolens* DSM 1800 (see WO 2009/076122), *Neosartorya fischeri*, *Neurospora crassa*, *Penicillium aurantiogriseum* (see WO 2009/127729), and *Thielavia terrestris* (see WO 2010/053838 and WO 2010/065448).

As used herein, a coumaroyl esterase (EC 3.1.1.73) is any polypeptide which is capable of catalysing a reaction of the form: coumaroyl-saccharide+H(2)O=coumarate+saccharide. The saccharide may be, for example, an oligosaccharide or a polysaccharide. This enzyme may also be referred to as trans-4-coumaroyl esterase, trans-p-coumaroyl esterase, p-coumaroyl esterase or p-coumaric acid esterase. This enzyme also falls within EC 3.1.1.73 so may also be referred to as a feruloyl esterase.

As used herein, an α-galactosidase (EC 3.2.1.22) is any polypeptide which is capable of catalysing the hydrolysis of terminal, non-reducing α-D-galactose residues in α-D-galactosides, including galactose oligosaccharides, galactomannans, galactans and arabinogalactans. Such a polypeptide may also be capable of hydrolyzing α-D-fucosides. This enzyme may also be referred to as melibiase.

As used herein, a β-galactosidase (EC 3.2.1.23) is any polypeptide which is capable of catalysing the hydrolysis of terminal non-reducing β-D-galactose residues in β-D-galactosides. Such a polypeptide may also be capable of hydrolyzing α-L-arabinosides. This enzyme may also be referred to as exo-(1->4)-β-D-galactanase or lactase.

As used herein, a β-mannanase (EC 3.2.1.78) is any polypeptide which is capable of catalysing the random hydrolysis of 1,4-β-D-mannosidic linkages in mannans, galactomannans and glucomannans. This enzyme may also be referred to as mannan endo-1,4-β-mannosidase or endo-1,4-mannanase.

As used herein, a β-mannosidase (EC 3.2.1.25) is any polypeptide which is capable of catalysing the hydrolysis of terminal, non-reducing β-D-mannose residues in β-D-mannosides. This enzyme may also be referred to as mannanase or mannase.

As used herein, an endo-polygalacturonase (EC 3.2.1.15) is any polypeptide which is capable of catalysing the random hydrolysis of 1,4-α-D-galactosiduronic linkages in pectate and other galacturonans. This enzyme may also be referred to as polygalacturonase pectin depolymerase, pectinase, endopolygalacturonase, pectolase, pectin hydrolase, pectin polygalacturonase, poly-α-1,4-galacturonide glycanohydrolase, endogalacturonase; endo-D-galacturonase or poly(1,4-α-D-galacturonide) glycanohydrolase.

As used herein, a pectin methyl esterase (EC 3.1.1.11) is any enzyme which is capable of catalysing the reaction: pectin+n $H_2O$=n methanol +pectate. The enzyme may also be known as pectinesterase, pectin demethoxylase, pectin methoxylase, pectin methylesterase, pectase, pectinoesterase or pectin pectylhydrolase.

As used herein, an endo-galactanase (EC 3.2.1.89) is any enzyme capable of catalysing the endohydrolysis of 1,4-β-D-galactosidic linkages in arabinogalactans. The enzyme may also be known as arabinogalactan endo-1,4-β-galactosidase, endo-1,4-β-galactanase, galactanase, arabinogalactanase or arabinogalactan 4-β-D-galactanohydrolase.

As used herein, a pectin acetyl esterase is defined herein as any enzyme which has an acetyl esterase activity which catalyses the deacetylation of the acetyl groups at the hydroxyl groups of GalUA residues of pectin.

As used herein, an endo-pectin lyase (EC 4.2.2.10) is any enzyme capable of catalysing the eliminative cleavage of (1→4)-α-D-galacturonan methyl ester to give oligosaccharides with 4-deoxy-6-O-methyl-α-D-galact-4-enuronosyl groups at their non-reducing ends. The enzyme may also be known as pectin lyase, pectin trans-eliminase; endo-pectin lyase, polymethylgalacturonic transeliminase, pectin methyltranseliminase, pectolyase, PL, PNL or PMGL or (1→4)-6-O-methyl-α-D-galacturonan lyase.

As used herein, a pectate lyase (EC 4.2.2.2) is any enzyme capable of catalysing the eliminative cleavage of (1→4)-α-D-galacturonan to give oligosaccharides with 4-deoxy-α-D-galact-4-enuronosyl groups at their non-reducing ends. The enzyme may also be known polygalacturonic transeliminase, pectic acid transeliminase, polygalacturonate lyase, endopectin methyltranseliminase, pectate transeliminase, endogalacturonate transeliminase, pectic acid lyase, pectic lyase, α-1,4-D-endopolygalacturonic acid lyase, PGA lyase, PPase-N, endo-α-1,4-polygalacturonic acid lyase, polygalacturonic acid lyase, pectin trans-eliminase, polygalacturonic acid trans-eliminase or (1→4)-α-D-galacturonan lyase.

As used herein, an alpha rhamnosidase (EC 3.2.1.40) is any polypeptide which is capable of catalysing the hydrolysis of terminal non-reducing α-L-rhamnose residues in α-L-rhamnosides or alternatively in rhamnogalacturonan. This enzyme may also be known as α-L-rhamnosidase T, α-L-rhamnosidase N or α-L-rhamnoside rhamnohydrolase.

As used herein, exo-galacturonase (EC 3.2.1.82) is any polypeptide capable of hydrolysis of pectic acid from the non-reducing end, releasing digalacturonate. The enzyme may also be known as exo-poly-α-galacturonosidase, exopolygalacturonosidase or exopolygalacturanosidase.

As used herein, exo-galacturonase (EC 3.2.1.67) is any polypeptide capable of catalysing: (1,4-α-D-galacturonide)$_n$+$H_2O$=(1,4-α-D-galacturonide)$_{n-1}$+D-galacturonate. The enzyme may also be known as galacturan 1,4-α-galacturonidase, exopolygalacturonase, poly(galacturonate) hydrolase, exo-D-galacturonase, exo-D-galacturonanase, exopoly-D-galacturonase or poly(1,4-α-D-galacturonide) galacturonohydrolase.

As used herein, exopolygalacturonate lyase (EC 4.2.2.9) is any polypeptide capable of catalysing eliminative cleavage of 4-(4-deoxy-α-D-galact-4-enuronosyl)-D-galacturonate from the reducing end of pectate, i.e. de-esterified pectin. This enzyme may be known as pectate disaccharide-lyase, pectate exo-lyase, exopectic acid transeliminase, exopectate lyase, exopolygalacturonic acid-trans-eliminase, PATE, exo-PATE, exo-PGL or (1→4)-α-D-galacturonan reducing-end-disaccharide-lyase.

As used herein, rhamnogalacturonan hydrolase is any polypeptide which is capable of hydrolyzing the linkage between galactosyluronic acid and rhamnopyranosyl in an endo-fashion in strictly alternating rhamnogalacturonan structures, consisting of the disaccharide [(1,2-alpha-L-rhamnoyl-(1,4)-alpha-galactosyluronic acid].

As used herein, rhamnogalacturonan lyase is any polypeptide which is any polypeptide which is capable of cleaving α-L-Rhap-(1→4)-α-D-GalpA linkages in an endo-fashion in rhamnogalacturonan by beta-elimination.

As used herein, rhamnogalacturonan acetyl esterase is any polypeptide which catalyzes the deacetylation of the backbone of alternating rhamnose and galacturonic acid residues in rhamnogalacturonan.

As used herein, rhamnogalacturonan galacturonohydrolase is any polypeptide which is capable of hydrolyzing galacturonic acid from the non-reducing end of strictly alternating rhamnogalacturonan structures in an exo-fashion.

As used herein, xylogalacturonase is any polypeptide which acts on xylogalacturonan by cleaving the β-xylose substituted galacturonic acid backbone in an endo-manner. This enzyme may also be known as xylogalacturonan hydrolase.

As used herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

As used herein, endo-arabinanase (EC 3.2.1.99) is any polypeptide which is capable of catalysing endohydrolysis of 1,5-α-arabinofuranosidic linkages in 1,5-arabinans. The enzyme may also be known as endo-arabinase, arabinan endo-1,5-α-L-arabinosidase, endo-1,5-α-L-arabinanase, endo-α-1,5-arabanase; endo-arabanase or 1,5-α-L-arabinan 1,5-α-L-arabinanohydrolase.

"Protease" includes enzymes that hydrolyze peptide bonds (peptidases), as well as enzymes that hydrolyze bonds between peptides and other moieties, such as sugars (glycopeptidases). Many proteases are characterized under EC 3.4 and are suitable for use in the processes as described herein. Some specific types of proteases include, cysteine proteases including pepsin, papain and serine proteases including chymotrypsins, carboxypeptidases and metalloendopeptidases.

"Lipase" includes enzymes that hydrolyze lipids, fatty acids, and acylglycerides, including phospoglycerides, lipoproteins, diacylglycerols, and the like. In plants, lipids are used as structural components to limit water loss and pathogen infection. These lipids include waxes derived from fatty acids, as well as cutin and suberin.

"Ligninase" includes enzymes that can hydrolyze or break down the structure of lignin polymers. Enzymes that can break down lignin include lignin peroxidases, manganese peroxidases, laccases and feruloyl esterases, and other enzymes described in the art known to depolymerize or otherwise break lignin polymers. Also included are enzymes capable of hydrolyzing bonds formed between hemicellulosic sugars (notably arabinose) and lignin. Ligninases include but are not limited to the following group of enzymes: lignin peroxidases (EC 1.11.1.14), manganese peroxidases (EC 1.11.1.13), laccases (EC 1.10.3.2) and feruloyl esterases (EC 3.1.1.73).

"Hexosyltransferase" (2.4.1-) includes enzymes which are capable of catalysing a transferase reaction, but which can also catalyze a hydrolysis reaction, for example of cellulose and/or cellulose degradation products. An example of a hexosyltransferase which may be used is a β-glucanosyltransferase. Such an enzyme may be able to catalyze degradation of (1,3)(1,4)glucan and/or cellulose and/or a cellulose degradation product.

"Glucuronidase" includes enzymes that catalyze the hydrolysis of a glucuronoside, for example β-glucuronoside to yield an alcohol. Many glucuronidases have been characterized and may be suitable for use, for example β-glucuronidase (EC 3.2.1.31), hyaluronoglucuronidase (EC 3.2.1.36), glucuronosyl-disulfoglucosamine glucuronidase (3.2.1.56), glycyrrhizinate β-glucuronidase (3.2.1.128) or α-D-glucuronidase (EC 3.2.1.139).

Expansins are implicated in loosening of the cell wall structure during plant cell growth. Expansins have been proposed to disrupt hydrogen bonding between cellulose and other cell wall polysaccharides without having hydrolytic activity. In this way, they are thought to allow the sliding of cellulose fibers and enlargement of the cell wall. Swollenin, an expansin-like protein contains an N-terminal Carbohydrate Binding Module Family 1 domain (CBD) and a C-terminal expansin-like domain. As described herein, an expansin-like protein or swollenin-like protein may comprise one or both of such domains and/or may disrupt the structure of cell walls (such as disrupting cellulose structure), optionally without producing detectable amounts of reducing sugars.

A cellulose induced protein, for example the polypeptide product of the cip1 or cip2 gene or similar genes (see Foreman et al., J. Biol. Chem. 278(34), 31988-31997, 2003), a cellulose/cellulosome integrating protein, for example the polypeptide product of the cipA or cipC gene, or a scaffoldin or a scaffoldin-like protein. Scaffoldins and cellulose integrating proteins are multi-functional integrating subunits which may organize cellulolytic subunits into a multi-enzyme complex. This is accomplished by the interaction of two complementary classes of domain, i.e. a cohesion domain on scaffoldin and a dockerin domain on each enzymatic unit. The scaffoldin subunit also bears a cellulose-binding module (CBM) that mediates attachment of the cellulosome to its substrate. A scaffoldin or cellulose integrating protein may comprise one or both of such domains.

A catalase; the term "catalase" means a hydrogen-peroxide: hydrogen-peroxide oxidoreductase (EC 1.11.1.6 or EC 1.11.1.21) that catalyzes the conversion of two hydrogen peroxides to oxygen and two waters. Catalase activity can be determined by monitoring the degradation of hydrogen peroxide at 240 nm based on the following reaction: $2H_2O_2 \rightarrow 2H_2O+O_2$. The reaction is conducted in 50 mM phosphate pH 7.0 at 25° C. with 10.3 mM substrate ($H_2O_2$) and approximately 100 units of enzyme per ml. Absorbance is monitored spectrophotometrically within 16-24 seconds, which should correspond to an absorbance reduction from 0.45 to 0.4. One catalase activity unit can be expressed as one micromole of $H_2O_2$ degraded per minute at pH 7.0 and 25° C.

The term "amylase" as used herein means enzymes that hydrolyze alpha-1,4-glucosidic linkages in starch, both in amylose and amylopectin, such as alpha-amylase (EC 3.2.1.1), beta-amylase (EC 3.2.1.2), glucan 1,4-alpha-glucosidase (EC 3.2.1.3), glucan 1,4-alpha-maltotetraohydrolase (EC 3.2.1.60), glucan 1,4-alpha-maltohexaosidase (EC 3.2.1.98), glucan 1,4-alpha-maltotriohydrolase (EC 3.2.1.116) and glucan 1,4-alpha-maltohydrolase (EC 3.2.1.133), and enzymes that hydrolyze alpha-1,6-glucosidic linkages, being the branch-points in amylopectin, such as pullulanase (EC 3.2.1.41) and limit dextinase (EC 3.2.1.142). A composition for use in the processes as described herein may be composed of enzymes from (1) commercial suppliers; (2) cloned genes expressing enzymes; (3) broth (such as that resulting from growth of a microbial strain in media, wherein the strains secrete proteins and enzymes into the media; (4) cell lysates of strains grown as in (3); and/or (5) plant material expressing enzymes. Different enzymes in a composition of the invention may be obtained from different sources.

The enzymes can be produced either exogenously in microorganisms, yeasts, fungi, bacteria or plants, then isolated and added, for example, to lignocellulosic material. Alternatively, the enzyme may be produced in a fermentation that uses (pretreated) lignocellulosic material (such as corn stover or wheat straw) to provide nutrition to an organism that produces an enzyme(s). In this manner, plants that produce the enzymes may themselves serve as a lignocellulosic material and be added into lignocellulosic material.

In the uses and processes described herein, the components of the compositions described above may be provided concomitantly (i.e. as a single composition per se) or separately or sequentially.

In an embodiment the enzyme composition is a whole fermentation broth of a fungus, preferably a whole fermentation broth of a filamentous fungus, more preferably a whole fermentation broth of Rasamsonia. The whole fermentation broth can be prepared from fermentation of non-recombinant and/or recombinant filamentous fungi. In an embodiment the filamentous fungus is a recombinant filamentous fungus comprising one or more genes which can be homologous or heterologous to the filamentous fungus. In an embodiment, the filamentous fungus is a recombinant filamentous fungus comprising one or more genes which can be homologous or heterologous to the filamentous fungus wherein the one or more genes encode enzymes that can degrade a cellulosic substrate. The whole fermentation broth may comprise any of the polypeptides described above or any combination thereof.

Preferably, the enzyme composition is a whole fermentation broth wherein the cells are killed. The whole fermentation broth may contain organic acid(s) (used for killing the cells), killed cells and/or cell debris, and culture medium.

Generally, filamentous fungi are cultivated in a cell culture medium suitable for production of enzymes capable of hydrolyzing a cellulosic substrate. The cultivation takes place in a suitable nutrient medium comprising carbon and nitrogen sources and inorganic salts, using procedures known in the art. Suitable culture media, temperature ranges and other conditions suitable for growth and cellulase and/or hemicellulase and/or pectinase production are known in the art. The whole fermentation broth can be prepared by growing the filamentous fungi to stationary phase and maintaining the filamentous fungi under limiting carbon conditions for a period of time sufficient to express the one or more cellulases and/or hemicellulases and/or pectinases. Once enzymes, such as cellulases and/or hemicellulases and/or pectinases, are secreted by the filamentous fungi into the fermentation medium, the whole fermentation broth can be used. The whole fermentation broth of the present invention may comprise filamentous fungi. In some embodiments, the whole fermentation broth comprises the unfractionated contents of the fermentation materials derived at the end of the fermentation. Typically, the whole fermentation broth comprises the spent culture medium and cell debris present after the filamentous fungi is grown to saturation, incubated under carbon-limiting conditions to allow protein synthesis (particularly, expression of cellulases and/or hemicellulases and/or pectinases). In some embodiments, the whole fermentation broth comprises the spent cell culture medium, extracellular enzymes and filamentous fungi. In some embodiments, the filamentous fungi present in whole fermentation broth can be lysed, permeabilized, or killed using methods known in the art to produce a cell-killed whole fermentation broth. In an embodiment, the whole fermentation broth is a cell-killed whole fermentation broth, wherein the whole fermentation broth containing the filamentous fungi cells are lysed or killed. In some embodiments, the cells are killed by lysing the filamentous fungi by chemical and/or pH treatment to generate the cell-killed whole broth of a fermentation of the filamentous fungi. In some embodiments, the cells are killed by lysing the filamentous fungi by chemical and/or pH treatment and adjusting the pH of the cell-killed fermentation mix to a suitable pH. In an embodiment, the whole fermentation broth comprises a first organic acid component comprising at least one 1-5 carbon organic acid and/or a salt thereof and a second organic acid component comprising at least 6 or more carbon organic acid and/or a salt thereof. In an embodiment, the first organic acid component is acetic acid, formic acid, propionic acid, a salt thereof, or any combination thereof and the second organic acid component is benzoic acid, cyclohexanecarboxylic acid, 4-methylvaleric acid, phenylacetic acid, a salt thereof, or any combination thereof.

The term "whole fermentation broth" as used herein refers to a preparation produced by cellular fermentation that undergoes no or minimal recovery and/or purification. For example, whole fermentation broths are produced when microbial cultures are grown to saturation, incubated under carbon-limiting conditions to allow protein synthesis (e.g., expression of enzymes by host cells) and secretion into cell culture medium. Typically, the whole fermentation broth is unfractionated and comprises spent cell culture medium, extracellular enzymes, and microbial, preferably non-viable, cells.

If needed, the whole fermentation broth can be fractionated and the one or more of the fractionated contents can be used. For instance, the killed cells and/or cell debris can be removed from a whole fermentation broth to provide a composition that is free of these components.

The whole fermentation broth may further comprise a preservative and/or anti-microbial agent. Such preservatives and/or agents are known in the art.

The whole fermentation broth as described herein is typically a liquid, but may contain insoluble components, such as killed cells, cell debris, culture media components, and/or insoluble enzyme(s). In some embodiments, insoluble components may be removed to provide a clarified whole fermentation broth.

In an embodiment, the whole fermentation broth may be supplemented with one or more enzyme activities that are not expressed endogenously, or expressed at relatively low level by the filamentous fungi, to improve the degradation of the cellulosic substrate, for example, to fermentable sugars such as glucose or xylose. The supplemental enzyme(s) can be added as a supplement to the whole fermentation broth and the enzymes may be a component of a separate whole fermentation broth, or may be purified, or minimally recovered and/or purified.

In an embodiment, the whole fermentation broth comprises a whole fermentation broth of a fermentation of a recombinant filamentous fungus overexpressing one or more enzymes to improve the degradation of the cellulosic substrate. Alternatively, the whole fermentation broth can comprise a mixture of a whole fermentation broth of a fermentation of a non-recombinant filamentous fungus and a recombinant filamentous fungus overexpressing one or more enzymes to improve the degradation of the cellulosic substrate. In an embodiment, the whole fermentation broth comprises a whole fermentation broth of a fermentation of a filamentous fungus overexpressing beta-glucosidase. Alternatively, the whole fermentation broth for use in the present methods and reactive compositions can comprise a mixture of a whole fermentation broth of a fermentation of a non-recombinant filamentous fungus and a whole fermentation broth of a fermentation of a recombinant filamentous fungus overexpressing a beta-glucosidase.

Lignocellulosic material as used herein includes any lignocellulosic and/or hemicellulosic material. Lignocellulosic material suitable for use in the processes as described herein includes biomass, e.g. virgin biomass and/or non-virgin biomass such as agricultural biomass, commercial organics, construction and demolition debris, municipal solid waste, waste paper and yard waste. Common forms of biomass include trees, shrubs and grasses, wheat, wheat straw, sugar cane, cane straw, sugar cane bagasse, switch grass, miscanthus, energy cane, corn, corn stover, corn husks, corn cobs, corn fiber, corn kernels, canola stems, soybean stems, sweet sorghum, products and by-products from milling of grains such as corn, wheat and barley (including wet milling and dry milling) often called "bran or fibre", distillers dried grains, as well as municipal solid waste, waste paper and yard waste. The biomass can also be, but is not limited to, herbaceous material, agricultural residues, forestry residues, municipal solid wastes, waste paper, and pulp and paper mill residues. "Agricultural biomass" includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, fruit peels, vines, sugar beet pulp, wheat midlings, oat hulls, and hard and soft woods (not including woods with deleterious materials). In addition, agricultural biomass includes organic waste materials generated from agricultural processes including farming and forestry activities, specifically including forestry wood waste. Agricultural biomass may be any of the above-mentioned singularly or in any combination or mixture thereof.

In an embodiment the lignocellulosic material is pretreated before the enzymatic hydrolysis. Pretreatment is done by means of heat and chemical modification.

The lignocellulosic material is pretreated at a temperature of 155° C. to 220° C., preferably 160° C. to 200° C., more preferably 170° C. to 190° C.

The lignocellulosic material is pretreated at a pH of 1.0 to 2.5, preferably of 1.3 to 2.4, preferably of 1.6 to 2.3 and more preferably of 1.9 to 2.2.

The lignocellulosic material is pretreated for 0.5 to 20 minutes, preferably 1 to 15 minutes, preferably 2 to 10 minutes and more preferably 2.5 to 6 minutes.

The lignocellulosic material is pretreated is a pressure of 5 to 25 bara.

The lignocellulosic material may be washed. In an embodiment the lignocellulosic material may be washed after the pretreatment. The washing step may be used to remove water soluble compounds that may act as inhibitors for the fermentation and/or hydrolysis step. The washing step may be conducted in manner known to the skilled person. Next to washing, other detoxification methods do exist. The lignocellulosic material may also be detoxified by any (or any combination) of these methods which include, but are not limited to, solid/liquid separation, vacuum evaporation, extraction, adsorption, neutralization, overliming, addition of reducing agents, addition of detoxifying enzymes such as laccases or peroxidases, addition of microorganisms capable of detoxification of hydrolysates.

The enzyme composition used in the process as described herein can extremely effectively hydrolyze lignocellulosic material, for example corn stover, wheat straw, cane straw, and/or sugar cane bagasse, which can then be further converted into a product, such as ethanol, biogas, butanol, a plastic, an organic acid, a solvent, an animal feed supplement, a pharmaceutical, a vitamin, an amino acid, an enzyme or a chemical feedstock. Additionally, intermediate products from a process following the hydrolysis, for example lactic acid as intermediate in biogas production, can be used as building block for other materials.

In an embodiment the amount of enzyme added (herein also called enzyme dosage or enzyme load) is low. In an embodiment the amount of enzyme is 0.1-10 mg protein/g dry matter.

The pH during the enzymatic hydrolysis of the pretreated lignocellulosic material is 4 to 6. The temperature during the enzymatic hydrolysis of the pretreated lignocellulosic material is 50° C. to 65° C., preferably 55° C. to 65° C.

In an embodiment the hydrolysis step is conducted until 70%-90%, preferably 70%-95%, more preferably 70%-100% of available sugar in the lignocellulosic material is released.

The enzymatic hydrolysis of a process as described herein is carried out using pretreated lignocellulosic material having a dry matter weight of 15 to 25% (w/w).

As described above, the present invention also relates to a process for the preparation of a fermentation product from lignocellulosic material, comprising the steps of (a) performing a process for the preparation of a sugar product from lignocellulosic material as described above, (b) fermenting the sugar product to obtain the fermentation product; and (c) optionally, recovering the fermentation product. As described above, the sugar product can also be called hydrolysed lignocellulosic material.

In an embodiment the fermentation is done in a reactor. In an embodiment the fermentation may also be done in two, three, four, five, six, seven, eight, nine, ten or even more reactors. So, the term "reactor" is not limited to a single reactor, but may mean multiple reactors.

In an embodiment the fermentation is done in a reactor having a volume of 1-5000 m$^3$. In case multiple reactors are used in the fermentation of the processes as described herein, they may have the same volume, but also may have a different volume.

In an embodiment the reactor in which the fermentation is done has a ratio height to diameter of 2:1 to 8:1.

In an embodiment the fermentation is done by an alcohol producing microorganism to produce alcohol. The fermentation by an alcohol producing microorganism to produce alcohol can be done in the same reactor wherein the hydrolysis is performed. Preferably, the fermentation by an alcohol producing microorganism to produce alcohol is performed in a separate reactor. In an embodiment the fermentation is done by a yeast. In an embodiment the alcohol producing microorganism is a yeast. In an embodiment the alcohol producing microorganism is able to ferment at least a C5 sugar and at least a C6 sugar. In an embodiment the fermentation is done with a yeast that is able to convert at least one C5 sugar. In an embodiment the application relates to a process for the preparation of a fermentation product from lignocellulosic material, comprising the following steps: (a) pretreating the lignocellulosic material at a temperature of 160° C. to 200° C. at a pH of 1.0 to 2.5 for 1 to 15 minutes; (b) enzymatically hydrolysing the pretreated lignocellulosic material having a dry matter weight of 15 to 25% (w/w) at a temperature of 50° C. to 65° C. and a pH of 4 to 6 for 40 hours to 150 hours using a whole fermentation broth of a filamentous fungus, said broth comprising at least a cellobiohydrolase, an endoglucanase, a beta-glucosidase, a xylanase, a beta-xylosidase and a lytic polysaccharide monooxygenase, to obtain a hydrolysed lignocellulosic material; (c) fermenting the hydrolysed lignocellulosic material to produce a fermentation product; and (d) optionally, recovering the fermentation product, wherein the hydrolysed lignocellulosic material comprises glucose, galactose and arabinose. In an embodiment the hydrolysed lignocellulosic material comprises acetic acid, preferably 0.3% (w/w) or more. In an embodiment the hydrolysed lignocellulosic material comprises glycerol. In an embodiment the hydrolysed lignocellulosic material comprises acetic acid, glycerol and a C6 sugar and/or a C5 sugar. In an embodiment the microorganism used for the fermentation ferments acetic acid, glycerol and a C6 sugar and/or a C5 sugar to a fermentation product. In an embodiment the yeast used for the fermentation ferments acetic acid, glycerol and a C6 sugar and/or a C5 sugar to a fermentation product. In an embodiment the yeast used for the fermentation ferments acetic acid, glycerol and a C6 sugar and/or a C5 sugar to ethanol. In an embodiment the hydrolysed lignocellulosic material comprises $Mn^{2+}$.

In a further aspect, the application includes a process as described herein in which a microorganism is used for the fermentation of a carbon source comprising sugar(s), e.g. glucose, L-arabinose, galactose and/or xylose. The carbon source may include any carbohydrate oligo- or polymer comprising L-arabinose, galactose, xylose or glucose units, such as e.g. lignocellulose, xylans, cellulose, starch, arabinan and the like. For release of xylose or glucose units from such carbohydrates, appropriate carbohydrases (such as xylanases, glucanases, amylases and the like) may be added to the fermentation medium or may be produced by the modified host cell. In the latter case, the modified host cell may be genetically engineered to produce and excrete such carbohydrases. An additional advantage of using oligo- or polymeric sources of glucose is that it enables to maintain a low(er) concentration of free glucose during the fermentation, e.g. by using rate-limiting amounts of the carbohydrases. This, in turn, will prevent repression of systems required for metabolism and transport of non-glucose sugars such as xylose. In an embodiment the modified host cell ferments both the L-arabinose (optionally xylose) and glucose, preferably simultaneously in which case preferably a modified host cell is used which is insensitive to glucose repression to prevent diauxic growth. In addition to a source of L-arabinose, optionally xylose (and glucose) as carbon source, the fermentation medium will further comprise the appropriate ingredient required for growth of the modified host cell.

The fermentation process may be an aerobic or an anaerobic fermentation process. An anaerobic fermentation process is herein defined as a fermentation process run in the absence of oxygen or in which substantially no oxygen is consumed, preferably less than 5, 2.5 or 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem many microorganisms use pyruvate or one of its derivatives as an electron and hydrogen acceptor thereby regenerating $NAD^+$. Thus, in a preferred anaerobic fermentation process pyruvate is used as an electron (and hydrogen acceptor) and is reduced to fermentation products such as ethanol, lactic acid, 3-hydroxy-propionic acid, acrylic acid, acetic acid, succinic acid, citric acid, malic acid, fumaric acid, an amino acid, 1,3-propane-diol, ethylene, glycerol, butanol, a β-lactam antibiotic and a cephalosporin. In a preferred embodiment, the fermentation process is anaerobic. An anaerobic process is advantageous, since it is cheaper than aerobic processes: less special equipment is needed. Furthermore, anaerobic processes are expected to give a higher product yield than aerobic processes. Under aerobic conditions, usually the biomass yield is higher than under anaerobic conditions. As a consequence, usually under aerobic conditions, the expected product yield is lower than under anaerobic conditions.

In another embodiment the fermentation process is under oxygen-limited conditions. More preferably, the fermentation process is aerobic and under oxygen-limited conditions. An oxygen-limited fermentation process is a process in which the oxygen consumption is limited by the oxygen transfer from the gas to the liquid. The degree of oxygen limitation is determined by the amount and composition of the ingoing gas flow as well as the actual mixing/mass transfer properties of the fermentation equipment used. Preferably, in a process under oxygen-limited conditions, the rate of oxygen consumption is at least 5.5, more preferably at least 6 and even more preferably at least 7 mmol/L/h. In an embodiment the fermentation is anaerobic.

The fermentation process is preferably run at a temperature that is optimal for the microorganism used. Thus, for most yeasts or fungal cells, the fermentation process is performed at a temperature which is less than 42° C., preferably 38° C. or lower. For yeast or filamentous fungal host cells, the fermentation process is preferably performed at a temperature which is lower than 35, 33, 30 or 28° C. and at a temperature which is higher than 20, 22, or 25° C. In an embodiment the fermentation is performed between 25° C. and 35° C.

In an embodiment the fermentations are conducted with a fermenting microorganism. In an embodiment of the invention, the alcohol (e.g. ethanol) fermentations of C5 sugars are conducted with a C5 fermenting microorganism. In an embodiment of the invention, the alcohol (e.g. ethanol) fermentations of C6 sugars are conducted with a C5 fermenting microorganism or a commercial C6 fermenting microorganism. Commercially available yeast suitable for ethanol production include, but are not limited to, BIO-FERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In an embodiment the alcohol producing microorganism is a microorganism that is able to ferment at least one C5 sugar. Preferably, it also is able to ferment at least one C6 sugar. In an embodiment the application describes a process for the preparation of ethanol from lignocellulosic material, comprising the steps of (a) performing a process for the preparation of a sugar product from lignocellulosic material as described above, (b) fermentation of the sugar product to produce ethanol; and (c) optionally, recovery of the ethanol.

The fermentation can be done with a yeast that is able to ferment at least one C5 sugar.

The microorganism used in the fermentation may be a prokaryotic or eukaryotic organism. The microorganism used may be a genetically engineered microorganism. Examples of suitable microorganisms are yeasts, for instance *Saccharomyces*, e.g. *Saccharomyces cerevisiae*, *Saccharomyces pastorianus* or *Saccharomyces uvarum*, *Hansenula*, *Issatchenkia*, e.g. *Issatchenkia orientalis*, *Pichia*, e.g. *Pichia stipites* or *Pichia pastoris*, *Kluyveromyces*, e.g. *Kluyveromyces fagilis*, *Candida*, e.g. *Candida pseudotropicalis* or *Candida acidothermophilum*, *Pachysolen*, e.g. *Pachysolen tannophilus* or bacteria, for instance *Lactobacillus*, e.g. *Lactobacillus lactis*, *Geobacillus*, *Zymomonas*, e.g. *Zymomonas mobilis*, *Clostridium*, e.g. *Clostridium phytofermentans*, *Escherichia*, e.g. *E. coli*, *Klebsiella*, e.g. *Klebsiella oxytoca*. In an embodiment the microorganism that is able to ferment at least one C5 sugar is a yeast. In an embodiment, the yeast belongs to the genus *Saccharomyces*, preferably of the species *Saccharomyces cerevisiae*. The yeast, e.g. *Saccharomyces cerevisiae*, used in the processes as described herein is capable of converting hexose (C6) sugars and pentose (C5) sugars. The yeast, e.g. *Saccharomyces cerevisiae*, used in the processes as described herein can anaerobically ferment at least one C6 sugar and at least one C5 sugar. In an embodiment the yeast as described herein is capable of using L-arabinose and xylose in addition to glucose anaerobically. In an embodiment, the yeast is capable of converting L-arabinose into L-ribulose and/or xylulose 5-phosphate and/or into a desired fermentation product, for example into ethanol. Organisms, for example *Saccharomyces cerevisiae* strains, able to produce ethanol from L-arabinose may be produced by modifying a host yeast introducing the araA (L-arabinose isomerase), araB (L-ribuloglyoxalate) and araD (L-ribulose-5-P4-epimerase) genes from a suitable source. Such genes may be introduced into a host cell in order that it is capable of using arabinose. Such an approach is given is described in WO2003/095627. araA, araB and araD genes from *Lactobacillus plantarum* may be used and are disclosed in WO2008/041840. The araA gene from *Bacillus subtilis* and the araB and araD genes from *Escherichia coli* may be used and are disclosed in EP1499708. In another embodiment, araA, araB and araD genes may derived from of at least one of the genus *Clavibacter, Arthrobacter* and/or *Gramella*, in particular one of *Clavibacter michiganensis, Arthrobacter aurescens*, and/or *Gramella forsetii*, as disclosed in WO 2009011591. In an embodiment, the yeast may also comprise one or more copies of xylose isomerase gene and/or one or more copies of xylose reductase and/or xylitol dehydrogenase.

The yeast may comprise one or more genetic modifications to allow the yeast to ferment xylose. Examples of genetic modifications are introduction of one or more xylA-gene, XYL1 gene and XYL2 gene and/or XKS1-gene; deletion of the aldose reductase (GRE3) gene; overexpression of PPP-genes TA1, TKL1, RPE1 and RKI1 to allow the increase of the flux through the pentose phosphate pathway in the cell. Examples of genetically engineered yeast are described in EP1468093 and/or WO2006/009434.

An example of a suitable commercial yeast is RN1016 that is a xylose and glucose fermenting *Saccharomyces cerevisiae* strain from DSM, the Netherlands.

In an embodiment, the fermentation process for the production of ethanol is anaerobic. Anaerobic has already been defined earlier herein. In another embodiment, the fermentation process for the production of ethanol is aerobic. In another embodiment, the fermentation process for the production of ethanol is under oxygen-limited conditions, e.g. aerobic and under oxygen-limited conditions. Oxygen-limited conditions have already been defined earlier herein.

Alternatively, to the fermentation processes described above, at least two distinct cells may be used, this means this process is a co-fermentation process. All embodiments of the fermentation processes as described above are also embodiments of this co-fermentation process: identity of the fermentation product, identity of source of L-arabinose and source of xylose, conditions of fermentation (aerobic or anaerobic conditions, oxygen-limited conditions, temperature at which the process is being carried out, productivity of ethanol, yield of ethanol).

Fermentation products that may be produced by the processes of the invention can be any substance derived from fermentation. They include, but are not limited to, alcohol (such as arabinitol, butanol, ethanol, glycerol, methanol, 1,3-propanediol, sorbitol, and xylitol); organic acid (such as acetic acid, acetonic acid, adipic acid, ascorbic acid, acrylic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, maleic acid, malic acid, malonic acid, oxalic acid, oxaloacetic acid, propionic acid, succinic acid, and xylonic acid); ketones (such as acetone); amino acids (such as aspartic acid, glutamic acid, glycine, lysine, serine, tryptophan, and threonine); alkanes (such as pentane, hexane, heptane, octane, nonane, decane, undecane, and dodecane), cycloalkanes (such as cyclopentane, cyclohexane, cycloheptane, and cyclooctane), alkenes (such as pentene, hexene, heptene, and octene); and gases (such as methane, hydrogen ($H_2$), carbon dioxide ($CO_2$), and carbon monoxide (CO)). The fermentation product can also be a protein, a vitamin, a pharmaceutical, an animal feed supplement, a specialty chemical, a chemical feedstock, a plastic, a solvent, ethylene, an enzyme, such as a protease, a cellulase, an amylase, a glucanase, a lactase, a lipase, a lyase, an oxidoreductase, a transferase or a xylanase. In a preferred embodiment an alcohol is prepared in the fermentation processes as described herein. In a preferred embodiment ethanol is prepared in the fermentation processes as described herein.

The processes as described herein may comprise recovery of all kinds of products made during the processes including fermentation products such as ethanol. A fermentation product may be separated from the fermentation broth in manner know to the skilled person. Examples of techniques for recovery include, but are not limited to, chromatography, electrophoretic procedures, differential solubility, distillation, or extraction. For each fermentation product the skilled person will thus be able to select a proper separation technique. For instance, ethanol may be separated from a yeast fermentation broth by distillation, for instance steam distillation/vacuum distillation in conventional way.

In an embodiment the processes as described herein also produce energy, heat, electricity and/or steam.

EXAMPLES

Example 1

Conditions for Pretreatment and Enzymatic Hydrolysis of Lignocellulosic Material Corn stover (with a dry matter based composition of 36.5% (w/w) glucan, 0.2% (w/w) mannan, 1.0% (w/w) galactan, 2.3% (w/w) arabinan, 19.4% (w/w) xylan, 2.9%

(w/w) acetyl and 0.6% (w/w) formyl) was dried in an oven at 40° C. under vacuum to a moisture content of 9.3% (w/w). Thereafter, the dried material was milled into particles <2 mm and the milled material was used for further experiments.

A stirring bar, 0.83 gram of milled dried corn stover (=0.75 gram dry weight) and 9.17 gram sulphuric acid solution or water were added to 20 ml vials resulting in a corn stover concentration of 7.5% (w/w). The vials were stored overnight and thereafter subjected to a pretreatment step using a microwave (Biotage Initiator 2.0 Microwave synthesizer) under the following conditions:

TABLE 1

Pretreatment conditions.

| Sample number | Temperature (° C.) | Time (minutes) | pH |
|---|---|---|---|
| 1 | 160 | 4.6 | 1.3 |
| 2 | 180 | 2.7 | 1.9 |
| 3 | 200 | 1.9 | 2.5 |
| 4 | 140 | 151 | 1.9 |
| 5 | 200 | 15 | 4.0 |

* wt % sulphuric acid in samples 1-5 was 0.67, 0.32, 0.24, 0.32 and 0, respectively.

After pretreatment, the samples were subjected to enzymatic hydrolysis. The vials used for the pretreatment processes were opened and their content was transferred to a centrifuge tube of 40 ml. Subsequently, the pH of the pretreated samples was set to pH 4.5 using a 2 M solution of NaOH. The total volume NaOH solution added was used to correct the final dry matter content of each tube (the differently pretreated samples required different volumes of 2M NaOH to set the pH to 4.5 ranging from 0.05 ml to 0.5 ml). Next, a *Talaromyces emersoniicellulase* cocktail (i.e. a whole fermentation broth) containing 2.0% *Talaromyces emersonii* beta-glucosidase on total protein (w/w) was added to a final dosage of 30 mg protein per gram of dry matter. The cocktail was produced according to the inoculation and fermentation procedures described in WO 2011/000949. The protein concentration of the cocktail was determined using a TCA-biuret method. In short, bovine serum albumin (BSA) dilutions (0, 1, 2, 5, 8 and 10 mg/ml) were made to generate a calibration curve. Additionally, dilutions of the cocktail were made with water. Of each diluted sample (of the BSA and the cocktail), 270 µl was transferred into a 10-ml tube containing 830 µl of a 12% (w/v) trichloro acetic acid solution in acetone and mixed thoroughly. Subsequently, the tubes were incubated on ice water for one hour and centrifuged for 30 minutes at 4° C. and 6000 rpm. The supernatant was discarded and pellets were dried by inverting the tubes on a tissue and letting them stand for 30 minutes at room temperature. Next, 3 ml BioQuant Biuret reagent mix was added to the pellet in the tubes and the pellet was solubilized upon mixing followed by addition n of 1 ml water. The tubes were mixed thoroughly and incubated at room temperature for 30 minutes. The absorption of the mixtures was measured at 546 nm and a water sample was used as a blank measurement. Dilutions of the cocktail that gave an absorption value at 546 nm within the range of the calibration line were used to calculate the total protein concentration in the cocktail via the BSA calibration line.

Centrifuge tubes containing the pretreated material and the enzyme cocktail were incubated in an oven incubator at 62° C., while rotating. After incubation for 72 hours at pH 4.5, 62° C., the obtained hydrolysates were centrifuged and the glucose and xylose content of the supernatant was analyzed using a High-Performance Liquid Chromatography System (Agilent 1100) equipped with a refection index detector (Agilent 1260 Infinity). The separation of the sugars was achieved by using a 300×7.8 mm Aminex HPX-87P (Bio Rad) column containing a Micro Guard Carbo-P (Bio Rad) pre-column. The mobile phase was HPLC grade water, the flow rate was 0.6 ml/min and the column temperature was 85° C. The pre-column was kept at room temperature. The injection volume was 10 µl. The samples were diluted with HPLC grade water to an estimated maximum of 2 g/l glucose and filtered by using 0.2 µm filter (Afridisc LC25 mm syringe filter PVDF membrane). The glucose and xylose content was identified according to the retention time and quantified via a glucose and xylose calibration curve generated with glucose standards (D-(+)-Glucose, Sigma) ranging from 0.2; 0.4; 1.0; 2.0 g/l and xylose standards (xylose, Sigma) ranging from 0.2; 0.4; 1.0; 2.0 g/l. The results are shown in Table 2.

TABLE 2

Glucan, xylan and total conversion.

| Sample number | Glucan to glucose conversion (mol %) | Xylan to xylose conversion (mol %) | Total conversion of biomass to sugars (mol %) |
|---|---|---|---|
| 1 | 94 | 113 | 101 |
| 2 | 87 | 105 | 93 |
| 3 | 95 | 104 | 98 |
| 4 | 80 | 100 | 87 |
| 5 | 87 | 69 | 81 |

TABLE 3

Xylan degradation loss to furfural.

| Sample number | Furfural concentration (ppm)* | Xylan degradation loss to furfural (mol % of original xylan) |
|---|---|---|
| 1 | 210 | 2.0 |
| 2 | 150 | 1.4 |
| 3 | 340 | 3.2 |
| 4 | 750 | 7.1 |
| 5 | 470 | 4.4 |

*Furfural was measured by HPLC using an Aminex HPX-87H column (BioRad) at a temperature of 60° C. and an injection volume of 100 µl; Eluent: 5 mM $H_2SO_4$ at a flow of 0.55 ml/min; RI Detection: Detector temperature: 50° C.; Runtime: 60 min The data in Table 2 show that carrying out a process with pretreatment and hydrolysis conditions according to the instant invention (see samples 1-3) resulted in higher conversion rates than when a process was carried out with different pretreatment and hydrolysis conditions (see samples 4-5). When carrying out a process with pretreated lignocellulosic material having a dry matter weight of 15 to 25% (w/w) the difference in conversion rates between the process that is carried out with pretreatment and hydrolysis conditions according to the instant invention and a process that is carried out with different pretreatment and hydrolysis conditions is even larger (i.e. the process that is carried out with pretreatment and hydrolysis conditions according to the instant invention having higher conversion rates).

The data in Table 3 show that lower degradation losses of xylan to furfural are seen for samples that have been subjected to a process with pretreatment and hydrolysis conditions according to the instant invention (i.e. samples 1-3) compared to samples that have been subjected to different pretreatment and hydrolysis conditions (i.e. samples 4-5). The lowest degradation loss of xylan to furfural is seen for sample 2, i.e. a sample that ihas been subjected to pretreatment at a temperature of 170° C. to 190° C. and a pH of 1.9 to 2.2 for 2.5 to 6 minutes.

The invention claimed is:

1. A process for the preparation of preparing at least one sugar from lignocellulosic material, comprising:
   a) pretreating the lignocellulosic material at a temperature of 160° C. to 200° C. at a pH of 1.0 to 2.5 for 1 to 15 minutes;
   b) enzymatically hydrolysing the pretreated lignocellulosic material having a dry matter weight of 15 to 25% (w/w) at a temperature of 50° C. to 65° C. and a pH of 4 to 6 for 40 hours to 150 hours using a whole fermentation broth of a filamentous fungus, said broth comprising at least a cellobiohydrolase, an endoglucanase, a beta-glucosidase, a xylanase, a beta-xylosidase, and a lytic polysaccharide monooxygenase; and
   c) optionally, recovering the at least one sugar from the enzymatically hydrolysed pretreated lignocellulosic material, wherein the at least one sugar is selected from the group consisting of: glucose;
cellobiose; xylose; arabinose; galactose; fructose; mannose; rhamnose; ribose;
galacturonic acid; glucuronic acid; and combinations thereof.

2. A process for the preparation of a fermentation product from lignocellulosic material, comprising:
   a) pretreating the lignocellulosic material at a temperature of 160° C. to 200° C. at a pH of 1.0 to 2.5 for 1 to 15 minutes;
   b) enzymatically hydrolysing the pretreated lignocellulosic material having a dry matter weight of 15 to 25% (w/w) at a temperature of 50° C. to 65° C. and a pH of 4 to 6 for 40 hours to 150 hours using a whole fermentation broth of a filamentous fungus, said broth comprising at least a cellobiohydrolase, an endoglucanase, a beta-glucosidase, a xylanase, a beta-xylosidase and a lytic polysaccharide monooxygenase, to obtain a hydrolysed lignocellulosic material;
   c) fermenting the enzymatically hydrolysed pretreated lignocellulosic material to produce a fermentation product; and
   d) optionally, recovering the fermentation product,
   wherein the fermentation product is selected from the group consisting of: arabinitol; butanol; ethanol; glycerol; methanol; 1,3-propanediol; sorbitol; xylitol; acetic acid; acetonic acid; adipic acid; ascorbic acid; acrylic acid; citric acid; 2,5-diketo-D-gluconic acid; formic acid; fumaric acid; glucaric acid; gluconic acid; glucuronic acid; glutaric acid; 3-hydroxypropionic acid; itaconic acid; lactic acid; maleic acid; malic acid; malonic acid; oxalic acid; oxaloacetic acid; propionic acid; succinic acid; xylonic acid; acetone; aspartic acid; glutamic acid; glycine; lysine; serine; tryptophan; threonine; ethylene; a β-lactam antibiotic; a cephalosporin; pentane; hexane; heptane; octane; nonane; decane; undecane; dodecane; cyclopentane; cyclohexane; cycloheptane; cyclooctane; pentene; hexene; heptene; octene; methane; hydrogen ($H_2$); carbon dioxide ($CO_2$); carbon monoxide (CO); a protease; a cellulase; an amylase; a glucanase; a lactase; a lipase; a lyase; an oxidoreductase; a transferase; and a xylanase.

3. The process according to claim 1, wherein oxygen is added to the pretreated lignocellulosic material during the enzymatic hydrolysis.

4. The process according to claim 1, wherein the enzymatic hydrolysis is performed in a reactor having a volume of 10-5000 $m^3$.

5. The process according to claim 1, wherein the enzymatic hydrolysis is conducted at a temperature of 55° C. to 65° C.

6. The process according to claim 1, wherein the lignocellulosic material is pretreated at a pH of 1.0 to 1.5.

7. The process according to claim 1, wherein the lignocellulosic material is pretreated for 1 to 5 minutes.

8. The process according to claim 2, wherein the fermentation is performed with a yeast that is able to convert at least one C5 sugar.

9. The process according to claim 1, wherein the pretreating is performed in a reactor having a volume of 30-200 $m^3$.

10. The process according to claim 1, wherein the pretreating is performed in a reactor having a height to diameter ratio of 3:1 to 12:1.

11. The process according to claim 1, wherein the enzymatic hydrolysis is performed in a reactor having a height to diameter ratio of 2:1 to 8:1.

12. The process according to claim 2, wherein the fermentation is performed in a reactor having a height to diameter ratio of from 2:1 to 8:1.

13. The process according to claim 1, wherein the at least one sugar is glucose.

14. The process according to claim 1, wherein the at least one sugar is xylose.

15. The process according to claim 1, wherein the at least one sugar is arabinose.

16. The process according to claim 1, wherein the at least one sugar is glucose and xylose.

17. The process according to claim 1, wherein the at least one sugar is glucose, xylose, and arabinose.

18. The process according to claim 2, wherein the fermentation product is ethanol.

* * * * *